United States Patent
Kissell et al.

(10) Patent No.: US 11,976,025 B2
(45) Date of Patent: *May 7, 2024

(54) ACETONITRILE SEPARATION PROCESS

(71) Applicant: Ascend Performance Materials Operations LLC, Houston, TX (US)

(72) Inventors: Kyle Kissell, Houston, TX (US); Basil Michaels, Houston, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 336 days.

This patent is subject to a terminal disclaimer.

(21) Appl. No.: 17/466,880

(22) Filed: Sep. 3, 2021

(65) Prior Publication Data
US 2022/0073451 A1   Mar. 10, 2022

Related U.S. Application Data

(60) Provisional application No. 63/074,586, filed on Sep. 4, 2020.

(51) Int. Cl.
*C07C 253/34*   (2006.01)
*B01D 3/14*   (2006.01)

(52) U.S. Cl.
CPC .................. *C07C 253/34* (2013.01)

(58) Field of Classification Search
CPC .............. C07C 253/34; B01D 3/143
See application file for complete search history.

(56) References Cited

U.S. PATENT DOCUMENTS

| | | | |
|---|---|---|---|
| 4,308,108 A | 12/1981 | Higuchi et al. | |
| 4,362,603 A | 12/1982 | Presson et al. | |
| 6,780,289 B2 | 8/2004 | Godbole | |
| 2020/0157044 A1 | 5/2020 | Michael et al. | |

FOREIGN PATENT DOCUMENTS

| | | |
|---|---|---|
| EP | 0937707 B1 | 4/2003 |
| WO | 02/06212 A2 | 1/2002 |

*Primary Examiner* — Sikarl A Witherspoon
(74) *Attorney, Agent, or Firm* — COZEN O'CONNOR

(57) ABSTRACT

Provided herein are processes for the separation of acetonitrile from low-purity feedstock streams. The provided processes are particularly useful for isolating acetonitrile at high purity from chemical manufacturing waste streams that include methanol, water, and allyl alcohol.

20 Claims, 1 Drawing Sheet

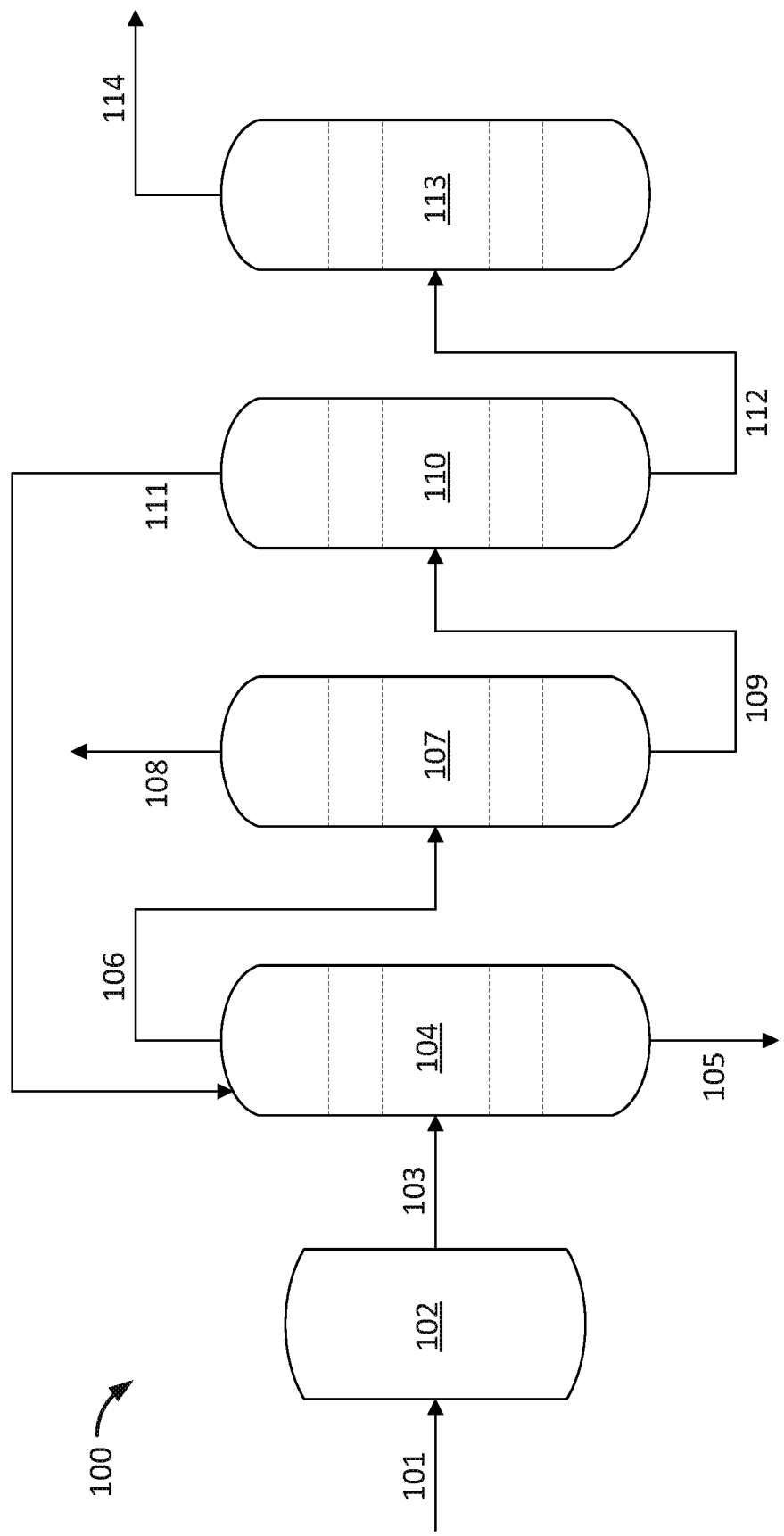

ACETONITRILE SEPARATION PROCESS

CROSS REFERENCE TO RELATED APPLICATIONS

This application claims priority to U.S. Provisional Application No. 63/074,586, filed Sep. 4, 2020, which is incorporated herein by reference.

FIELD

The present disclosure relates generally to downstream separation processes having the ability to isolate acetonitrile and which are particularly useful for the recovery of acetonitrile from industrial streams that include methanol and allyl alcohol.

BACKGROUND

Cyanocarbons, e.g., organic compounds having cyano functional groups, are known and are widely used in various applications. Many of these compounds, including acrylonitrile, are used as monomers to prepare various polymers, such as nylon, polyacrylonitrile, or acrylonitrile butadiene styrene. Several methods of producing cyanocarbons are known in the art, and these production methods often yield waste streams comprising small amounts of desirable co-products. For example, acetonitrile may be present in many of the conventional waste streams of industrial production processes. Typically, this co-product acetonitrile may be recovered using well-known separation schemes. These typical acrylonitrile process waste stream separation schemes, however, do not contemplate the presence of some other impurities in the waste streams, e.g., methanol, water, and/or allyl alcohol, which can complicate acetonitrile isolation due to, e.g., the formation of an azeotrope with acetonitrile.

A number of processes for recovering acetonitrile are known in the art. For example, U.S. Pat. No. 4,362,603 discloses a process for recovering an acetonitrile byproduct from a stream comprising acetonitrile, water, hydrogen cyanide, acrylonitrile, and other organics such as oxazole, allyl alcohol, acetone, or propionitrile by distilling in three distillation zones at varying pressures.

As another example, U.S. Pat. No. 6,780,289 discloses a method for the purification of crude acetonitrile comprising distilling the crude acetonitrile in a first fractional distillation column at below atmospheric pressure, withdrawing a first side draw fraction comprising acetonitrile, distilling the first side draw fraction in a second fractional distillation column at super atmospheric pressure, and withdrawing from the second distillation a second side draw fraction comprising purified acetonitrile.

While these references may relate to acetonitrile separation, these references fail to contemplate the challenges of recovering acetonitrile from feedstock streams that comprise particular concentrations of, for example, methanol, water, and/or allyl alcohol. Thus, the need exists for improved processes having more effective separation and/or recovery of by-product acetonitrile from methanol-, water-, and allyl alcohol-containing production process waste streams.

SUMMARY

In one aspect, the disclosure is to a process for producing acetonitrile. The process includes treating a feedstock stream containing acetonitrile, methanol, hydrogen cyanide, and water to remove hydrogen cyanide and produce an intermediate acetonitrile stream including less than 1 wt % hydrogen cyanide. In some embodiments, the feedstock stream includes more than 0.7 wt % methanol. In some embodiments, the treating includes digesting the feedstock stream in a digester, wherein sodium hydroxide and the feedstock stream are fed to the digester.

The method further includes distilling the intermediate acetonitrile stream in a first distillation column to yield a first bottoms stream containing water, and a first distillate stream containing acetonitrile. The first distillation column is operated at a pressure less than 150 kPa. In some embodiments, the first distillation column is operated at a pressure less than 80 kPa. In some embodiments the feedstock stream includes more than 50 wt % water and the first distillate stream includes less than 45 wt % water. In some embodiments, the mass ratio of the acetonitrile in the first distillate stream to the water in the first distillate stream is greater than 3:1. In some embodiments, the first bottoms stream and the first distillate stream each comprise methanol, and wherein the mass ratio of the methanol in the first bottoms stream to the methanol in the first distillate stream ranges from 0.4:1 to 10:1.

In some embodiments, the feedstock stream and the first bottoms stream each further include allyl alcohol. In some embodiments, the first bottoms stream includes from 0 to 1 wt % allyl alcohol. In some embodiments, the feedstock stream includes more than 0.05 wt % allyl alcohol and the first distillate stream includes less than 0.05 wt % allyl alcohol. In some embodiments, the mass ratio of the acetonitrile in the first distillate stream to the allyl alcohol in the first distillate stream is greater than 1000:1.

In some embodiments, the feedstock stream and the first distillate stream each further include oxazole. In some embodiments, the feedstock stream includes more than 0.09 wt % oxazole and the first bottoms includes less than 0.1 wt % oxazole. In some embodiments, the feedstock stream further includes acrylonitrile. In some embodiments, the feedstock stream further includes propionitrile.

The method further includes purifying the first distillate stream to yield a product acetonitrile stream and a recycle stream. In some embodiments, the product acetonitrile stream includes more than 98 wt % acetonitrile. In some embodiments the purifying includes distilling the first distillate stream in a second distillation column to yield a second distillate stream comprising methanol, and a second bottoms stream comprising acetonitrile, wherein the second distillation column is operated at a pressure less than 200 kPa. In some embodiments, the purifying further includes distilling the second bottoms stream in a third distillation column to yield the recycle stream comprising acetonitrile, and a third bottoms stream comprising acetonitrile, wherein the third distillation column is operated at a pressure less than 550 kPa. In some embodiments, the purifying further includes distilling the third bottoms stream in a fourth distillation column to yield the product acetonitrile stream, wherein the fourth distillation column is operated at a pressure less than 80 kPa.

BRIEF DESCRIPTION OF DRAWINGS

The present disclosure is described in detail below with reference to the appended drawings, wherein like numerals designate similar parts.

FIG. 1 is a schematic illustration of a process for recovering acetonitrile in accordance with an embodiment.

DETAILED DESCRIPTION

The present disclosure generally relates to acetonitrile separation processes that, when employed for example to isolate acetonitrile from industrial waste streams, provide advantageous improvements in producing an acetonitrile product stream at high purity and yield. For example, it would be beneficial for an acetonitrile separation process to have the ability to isolate acetonitrile from other components of an industrial waste stream, such as methanol, water, hydrogen cyanide, and allyl alcohol. These components are commonly present in, for example, waste streams from acrylonitrile production processes that use methanol to favor the production of hydrogen cyanide and to contribute to acrylonitrile production efficiencies.

It has been difficult, however, for conventional acetonitrile separation processes to effectively isolate acetonitrile from contaminating components that include methanol, water, hydrogen cyanide, and allyl alcohol. One reason for this is that some components, such as methanol, can detrimentally create azeotropes during distillation steps. This azeotrope formation in conventional separation processes can lead to significant problems that include reduced separation efficiencies, poor final acetonitrile product purities, and lower acetonitrile product yields. Other impurities in the feedstock stream can, due to their chemical structures and physical properties, also complicate the isolation of acetonitrile from the feedstock at purities and/or yields necessary for certain downstream applications.

As disclosed herein, the operation of one or more distillation columns of the provided acetonitrile separation process at lower pressures can result in an increase in the overall effectiveness of the process. Such lower operating pressures are not typically used in similar conventional acetonitrile separation processes as the increased vacuum requirements and accompanying increased chilling requirements for the distillations lead to higher costs and lower availabilities for these unit operations. Beneficially, any negative effects related to these distillation cost and availability issues are more than outweighed by benefits related to resulting increases in, e.g., the purity and/or yield of the final isolated acetonitrile product, and decreases in column operating times required to achieve these improved acetonitrile product specifications. Notably, the importance of lower distillation pressures in combination with other process parameters disclosed herein had not been previously appreciated.

Processes

In one aspect, a process for isolating acetonitrile from a low-purity acetonitrile feedstock stream is disclosed. The acetonitrile of the feedstock stream has a low purity due to the presence of significant concentrations of other components, including methanol, water, and hydrogen cyanide. The low purity of the acetonitrile in the feedstock stream can also be due to the presence of allyl alcohol, oxazole, and/or propionitrile in the stream. The provided acetonitrile separation process includes treating this feedstock stream to remove at least a portion of the hydrogen cyanide and produce an intermediate acetonitrile stream, distilling this intermediate acetonitrile stream to remove at least a portion of the water and produce a first distillate stream, and purifying this first distillate stream to yield a product acetonitrile stream including at least a portion of the acetonitrile at high purity.

Feedstock Stream

The feedstock stream of the provided separation process includes, inter alia, acetonitrile, methanol, hydrogen cyanide, and water. The feedstock stream can include one or more waste streams from other industrial chemical processes, e.g., the production of acrylonitrile, allyl cyanide, butyronitrile, polyacrylonitrile, polyamides, polyaramids, or combinations thereof. For example, waste streams from multiple processes for producing organic nitriles or derivatives thereof can be combined to form the feedstock stream. In some embodiments, the feedstock stream includes one or more waste streams, e.g., purge streams, from an acrylonitrile production process. In conventional acryonitrile production processes, acetonitrile-containing waste streams are burned in waste heat boilers to suppress the formation of nitrogen oxides. This solution, however, fails to capture the by-product acetonitrile. In the processes disclosed herein, however, these waste streams can be processed to recover the acetonitrile, preferably in at a high purity level.

In some embodiments, the concentration of acetonitrile in the feedstock stream ranges from 1.7 wt % to 30 wt %, e.g., from 1.7 wt % to 9.5 wt %, from 2.3 wt % to 13 wt %, from 3 wt % to 17 wt %, from 4 wt % to 23 wt %, or from 5.4 wt % to 30 wt %. In terms of upper limits, the acetonitrile concentration in the feedstock stream can be less than 30 wt %, e.g., less than 23 wt %, less than 17 wt %, less than 13 wt %, less than 9.5 wt %, less than 7.1 wt %, less than 5.4 wt %, less than 4 wt %, less than 3 wt %, or less than 2.3 wt %. In terms of lower limits, the acetonitrile concentration in the feedstock stream can be greater than 1.7 wt %, e.g., greater than 2.3 wt %, greater than 3 w %, greater than 4 wt %, greater than 5.4 wt %, greater than 7.1 wt %, greater than 9.5 wt %, greater than 13 wt %, greater than 17 wt %, or greater than 23 wt %. In some embodiments, higher acetonitrile concentrations, e.g., greater than 30 wt %, and lower acetonitrile concentrations, e.g., less than 1.7 wt %, may also be contemplated.

In some embodiments, the concentration of methanol in the feedstock stream ranges from 0.7 wt % to 15 wt %, e.g., from 0.7 wt % to 4.4 wt %, from 1 wt % to 6 wt %, from 1.3 wt % to 8.1 wt %, from 1.8 wt % to 11 wt % or from 2.4 wt % to 15 wt %. In terms of upper limits, the methanol concentration in the feedstock stream can be less than 15 wt %, e.g., less than 11 wt %, less than 8.1 wt %, less than 6 wt %, less than 4.4 wt %, less than 3.2 wt %, less than 2.4 wt %, less than 1.8 wt %, less than 1.3 wt %, or less than 1 wt %. In terms of lower limits, the methanol concentration in the feedstock stream can be greater than 0.7 wt %, e.g., greater than 1 wt %, greater than 1.3 wt %, greater than 1.8 wt %, greater than 2.4 wt %, greater than 3.2 wt %, greater than 4.4 wt %, greater than 6 wt %, greater than 8.1 wt %, or greater than 11 wt %. In some embodiments, higher methanol concentrations, e.g., greater than 15 wt %, and lower methanol concentrations, e.g., less than 0.7 wt %, may also be contemplated.

In some embodiments, the concentration of hydrogen cyanide in the feedstock stream ranges from 0.11 wt % to 2.7 wt %, e.g., from 0.11 wt % to 0.75 wt %, from 0.15 wt % to 1 wt %, from 0.21 wt % to 1.4 wt %, from 0.29 wt % to 2 wt %, or from 0.4 wt % to 2.7 wt %. In terms of upper limits, the hydrogen cyanide concentration in the feedstock stream can be less than 2.7 wt %, e.g., less than 2 wt %, less than 1.4 wt %, less than 1 wt %, less than 0.75 wt %, less than 0.55 wt %, less than 0.4 wt %, less than 0.29 wt %, less than 0.21 wt %, or less than 0.15 wt %. In terms of lower limits, the hydrogen cyanide concentration in the feedstock stream can be greater than 0.11 wt %, e.g., greater than 0.15 wt %, greater than 0.21 wt %, greater than 0.29 wt %, greater than 0.4 wt %, greater than 0.55 wt %, greater than 1 wt %, greater than 1.4 wt %, or greater than 2 wt %. In some embodiments, higher hydrogen cyanide concentrations, e.g., greater than 2.7 wt %, and lower hydrogen cyanide concentrations, e.g., less than 0.11 wt %, may also be contemplated.

In some embodiments, the concentration of water in the feedstock stream ranges from 50 wt % to 95 wt %, e.g., from 72 wt % to 92 wt %, from 72 wt % to 84 wt %, from 74 wt % to 86 wt %, from 76 wt % to 88 wt %, from 78 wt % to 90 wt %, or from 80 wt % to 92 wt %. In terms of upper limits, the water concentration in the feedstock stream can be less than 92 wt %, e.g., less than 90 wt %, less than 88 wt %, less than 86 wt %, less than 84 wt %, less than 82 wt %, less than 80 wt %, less than 78 wt %, less than 76 wt %, less than 74 wt %, or less than 72 wt %. In terms of lower limits, the water concentration in the feedstock stream can be greater than 50 wt %, e.g., greater than 72 wt %, greater than 74 wt %, greater than 76 wt %, greater than 78 wt %, greater than 80 wt %, greater than 82 wt %, greater than 84 wt %, greater than 86 wt %, greater than 88 wt %, or greater than 90 wt %. In some embodiments, higher water concentrations, e.g., greater than 92 wt %, and lower water concentrations, e.g., less than 50 wt %, may also be contemplated.

In some embodiments, the feedstock stream further includes allyl alcohol. The concentration of allyl alcohol in the feedstock stream can range, from example, from 0.05 wt % to 1.1. wt %, e.g., from 0.05 wt % to 0.32 wt %, from 0.068 wt % to 0.44 wt %, from 0.093 wt % to 0.59 wt %, from 0.13 wt % to 0.81 wt %, or from 0.17 wt % to 1.1 wt %. In terms of upper limits, the allyl alcohol concentration in the feedstock stream can be less than 1.1 wt %, e.g., less than 0.81 wt %, less than 0.59 wt %, less than 0.44 wt %, less than 0.32 wt %, less than 0.23 wt %, less than 0.17 wt %, less than 0.13 wt %, less than 0.093 wt %, or less than 0.068 wt %. In terms of lower limits, the allyl alcohol concentration in the feedstock stream can be greater than 0.05 wt %, e.g., greater than 0.068 wt %, greater than 0.093 wt %, greater than 0.13 wt %, greater than 0.17 wt %, greater than 0.23 wt %, greater than 0.32 wt %, greater than 0.44 wt %, greater than 0.59 wt %, or greater than 0.81 wt %. In some embodiments, higher allyl alcohol concentrations, e.g., greater than 1.1 wt %, and lower allyl alcohol concentrations, e.g., less than 0.05 wt %, may also be contemplated.

In some embodiments, the feedstock stream further includes oxazole. The concentration of oxazole in the feedstock stream can range, for example, from 0.09 wt % to 2.2 wt %, e.g., from 0.09 wt % to 0.61 wt %, from 0.12 wt % to 0.84 wt %, from 0.17 wt % to 1.2 wt %, from 0.23 wt % to 1.6 wt %, or from 0.32 wt % to 2.2 wt %. In terms of upper limits, the oxazole concentration in the feedstock stream can be less than 2.2 wt %, e.g., less than 1.6 wt %, less than 1.2 wt %, less than 0.84 wt %, less than 0.61 wt %, less than 0.44 wt %, less than 0.32 wt %, less than 0.23 wt %, less than 0.17 wt %, or less than 0.12 wt %. In terms of upper limits, the oxazole concentration in the feedstock stream can be greater than 0.09 wt %, e.g., greater than 0.12 wt %, greater than 0.17 wt %, greater than 0.23 wt %, greater than 0.32 wt %, greater than 0.44 wt %, greater than 0.61 wt %, greater than 0.84 wt %, greater than 1.2 wt %, or greater than 1.6 wt %. In some embodiments, higher oxazole concentrations, e.g., greater than 2.2 wt %, and lower oxazole concentrations, e.g., less than 0.09 wt %, may also be contemplated.

In some embodiment, the feedstock stream further includes acrylonitrile. The concentration of acrylonitrile in the feedstock stream can range, for example, from 0.05 wt % to 1.1. wt %, e.g., from 0.05 wt % to 0.32 wt %, from 0.068 wt % to 0.44 wt %, from 0.093 wt % to 0.59 wt %, from 0.13 wt % to 0.81 wt %, or from 0.17 wt % to 1.1 wt %. In terms of upper limits, the acrylonitrile concentration in the feedstock stream can be less than 1.1 wt %, e.g., less than 0.81 wt %, less than 0.59 wt %, less than 0.44 wt %, less than 0.32 wt %, less than 0.23 wt %, less than 0.17 wt %, less than 0.13 wt %, less than 0.093 wt %, or less than 0.068 wt %. In terms of lower limits, the acrylonitrile concentration in the feedstock stream can be greater than 0.05 wt %, e.g., greater than 0.068 wt %, greater than 0.093 wt %, greater than 0.13 wt %, greater than 0.17 wt %, greater than 0.23 wt %, greater than 0.32 wt %, greater than 0.44 wt %, greater than 0.59 wt %, or greater than 0.81 wt %. In some embodiments, higher acrylonitrile concentrations, e.g., greater than 1.1 wt %, and lower acrylonitrile concentrations, e.g., less than 0.05 wt %, may also be contemplated.

In some embodiments, the feedstock stream further includes propionitrile. The concentration of propionitrile in the feedstock stream can range, for example, from 0.05 wt % to 1.1. wt %, e.g., from 0.05 wt % to 0.32 wt %, from 0.068 wt % to 0.44 wt %, from 0.093 wt % to 0.59 wt %, from 0.13 wt % to 0.81 wt %, or from 0.17 wt % to 1.1 wt %. In terms of upper limits, the propionitrile concentration in the feedstock stream can be less than 1.1 wt %, e.g., less than 0.81 wt %, less than 0.59 wt %, less than 0.44 wt %, less than 0.32 wt %, less than 0.23 wt %, less than 0.17 wt %, less than 0.13 wt %, less than 0.093 wt %, or less than 0.068 wt %. In terms of lower limits, the propionitrile concentration in the feedstock stream can be greater than 0.05 wt %, e.g., greater than 0.068 wt %, greater than 0.093 wt %, greater than 0.13 wt %, greater than 0.17 wt %, greater than 0.23 wt %, greater than 0.32 wt %, greater than 0.44 wt %, greater than 0.59 wt %, or greater than 0.81 wt %. In some embodiments, higher propionitrile concentrations, e.g., greater than 1.1 wt %, and lower propionitrile concentrations, e.g., less than 0.05 wt %, may also be contemplated.

In some embodiments, the feedstock stream further includes one or more other impurities, typically in small concentrations, e.g., ppm or ppb. These impurities can include, for example, various waste products that result from the production of organic nitriles and derivatives thereof. For example, the feedstock stream can include one or more acrylamides, azoles, aliphatic nitriles, aromatic nitriles, alcohols, aldehydes, acrolein, fumarin, acrylamide, cyanide salts, acetone, derivatives thereof, or a combination thereof.

Feedstock Treatment

The feedstock stream of the provided separation is first treated to remove at least a portion of the hydrogen cyanide from the feedstock stream, producing an intermediate acetonitrile stream that does not include the hydrogen cyanide removed in the treatment. In some embodiments, the treating includes digesting the feedstock stream in a digester that is fed a strong base and the feedstock stream. In some embodiments, the strong base includes one or more metal hydroxides. The strong base can include, for example, sodium hydroxide, potassium hydroxide, magnesium hydroxide, calcium hydroxide, or a combination thereof. In some embodiments, the one or more metal hydroxides include sodium hydroxide. In some embodiments, the digester is fed another caustic solution in addition to or in place of the strong base. The other caustic solution can include, for example, one or more aldehydes. In some embodiments, the one or more aldehydes include formaldehyde.

In some embodiments, the concentration of hydrogen cyanide in the intermediate acetonitrile stream ranges from 0 to 1 wt %, e.g., from 0 to 0.16 wt %, from 0.016 wt % to 0.25 wt %, from 0.025 wt % to 0.4 wt %, from 0.04 wt % to 0.63 wt %, or from 0.063 wt % to 1 wt %. In terms of upper limits, the hydrogen cyanide concentration in the intermediate acetonitrile stream can be less than 1 wt %, e.g., less than 0.63 wt %, less than 0.4 wt %, less than 0.25 wt %, less than 0.16 wt %, less than 0.1 wt %, less than 0.063 wt %, less than 0.04 wt %, less than 0.025 wt %, or less than 0.016 wt %. In some cases, the component concentrations of the intermediate acetonitrile stream are similar to those of the feedstock stream, less the hydrogen cyanide removed, and the aforementioned ranges and limits are applicable. These component concentrations can be easily calculated by one of ordinary skill in the art.

First Distillation

The intermediate acetonitrile stream of the provided separation process is distilled in a first distillation column to yield a first bottoms stream and a first distillate stream. The first bottoms stream includes at least a portion of the water from the intermediate acetonitrile stream. The first distillate stream includes at least a portion of the acetonitrile from the intermediate acetonitrile stream.

In some embodiments, the first distillation column is operated at a pressure ranging from 5 kPa to 150 kPa, e.g., from 5 kPa to 130 kPa, from 5 kPa to 110 kPa, from 10 kPa to 80 kPa, from 10 kPa to 52 kPa, from 17 kPa to 59 kPa, from 24 kPa to 66 kPa, from 31 kPa to 73 kPa, or from 38 kPa to 80 kPa. In terms of upper limits, the first distillation column operating pressure can be less than 150 kPa, e.g., less than 130 kPa, less than 120 kPa, less than 110 kPa, less than 80 kPa, less than 73 kPa, less than 66 kPa, less than 59 kPa, less than 52 kPa, less than 45 kPa, less than 38 kPa, less than 31 kPa, less than 24 kPa, less than 17 kPa, or less than 10 kPa. In terms of lower limits, the first distillation column operating pressure can be greater than 5 kPa, e.g., greater than 10 kPa, greater than 17 kPa, greater than 24 kPa, greater than 31 kPa, greater than 38 kPa, greater than 45 kPa, greater than 52 kPa, greater than 59 kPa, greater than 66 kPa, greater than 73 kPa, or greater than 85 kPa. In some embodiments, higher column pressures, e.g., greater than 150 kPa, and lower column pressures, e.g., less than 5 kPa, may also be contemplated. Operation at these pressures, in some cases, provides for the aforementioned benefits.

In some embodiments, the first distillation column is operated at a temperature ranging from 20° C. to 90° C., e.g., from 65° C. to 90° C., from 65° C. to 80° C., from 67.5° C. to 82.5° C., from 70° C. to 85° C., from 72.5° C. to 87.5° C., or from 75° C. to 90° C. In terms of lower limits, the first distillation column operating temperature can be less than 90° C., e.g., less than 87.5° C., less than 85° C., less than 82.5° C., less than 80° C., less than 77.5° C., less than 75° C., less than 72.5° C., less than 70° C., less than 67.5° C., or less than 65° C. In terms of lower limits, the first distillation column operating temperature can be greater than 20° C., e.g., greater than 65° C., greater than 67.5° C., greater than 70° C., greater than 72.5° C., greater than 75° C., greater than 77.5° C., greater than 80° C., greater than 82.5° C., greater than 85° C., or greater than 87.5° C. In some embodiments, higher column temperatures, e.g., greater than 90° C., and lower column temperatures, e.g., less than 20° C., may also be contemplated.

The structure of the first distillation column can vary widely according to designs known to those of ordinary skill in the art, and any suitable column can be employed as long as the separation specifications described herein are achieved. For example the first distillation column can include any suitable separation device or combination of separation devices. The first distillation column can include a column, e.g., a standard distillation column, an extractive distillation column and/or an azeotropic distillation column. In some cases, the term "first distillation column" refers to multiple distillation columns configured to operate in conjunction with one another.

The first distillation column is configured to operate at a low pressure selected to provide the separation specifications disclosed herein. In some embodiments, the low pressure operation of the first distillation requirement is at a pressure not requiring the use of chilled water to maintain the needed vacuum. Theses embodiments can thus include additional operational expense savings through the use of non-chilled process water. In some embodiments, the low pressure operation of the first distillation column includes applying cooling to better enable the creation of a stronger vacuum. In some embodiments, the cooling includes delivering chilled water to the unit operation of the first distillation column.

In some embodiments, the first bottoms stream includes at least a portion of the water from the intermediate acetonitrile stream, such that the concentration of water in the first distillate stream is less than that in the intermediate acetonitrile stream. It can be beneficial for the provided separation process to remove much of the water of the intermediate acetonitrile stream in the first distillation, rather than in later unit operations, to realize energy and cost efficiencies, and to provide a final acetonitrile product stream having a higher acetonitrile product purity. The concentration of water in the first bottoms stream can range, for example, from, from 64 wt % to 99 wt %, e.g., from 64 wt % to 96 wt %, from 75 wt % to 97 wt %, from 82 wt % to 98 wt %, from 88 wt % to 98.6 wt %, or from 91 wt % to 99 wt %. In terms of upper limits, the water concentration in the first bottoms stream can be less than 99 wt %, e.g., less than 98.6 wt %, less than 98 wt %, less than 97 wt %, less than 96 wt %, less than 94 wt %, less than 91 wt %, less than 88 wt %, less than 82 wt %, or less than 75 wt %. In terms of lower limits, the water concentration in the first bottoms stream can be greater than 64 wt %, e.g., greater than 75 wt %, greater than 82 wt %, greater than 88 wt %, greater than 91 wt %, greater than 94 wt %, greater than 96 wt %, greater than 97 wt %, greater than 99 wt %, or greater than 98.6 wt %. In some embodiments, higher water concentrations, e.g., greater than 99 wt %, and lower water concentrations, e.g., less than 64 wt %, may also be contemplated.

In some embodiments the concentration of water in the first distillate stream ranges from 2.5 wt % to 45 wt %, e.g., from 2.5 wt % to 14 wt %, from 3.3 wt % to 19 wt %, from 4.5 wt % to 25 wt %, from 6 wt % to 34 wt %, or from 7.9 wt % to 45 wt %. In terms of upper limits, the water concentration in the first distillate stream can be less than 45 wt %, e.g., less than 33.7 wt %, less than 25 wt %, less than 19 wt %, less than 14 wt %, less than 11 wt %, less than 7.9 wt %, less than 6 wt %, less than 4.5 wt %, or less than 3.3 wt %. In terms of lower limits, the water concentration in the first distillate stream can be greater than 2.5 wt %, e.g., greater than 3.3 wt %, greater than 4.5 wt %, greater than 6 wt %, greater than 7.9 wt %, greater than 11 wt %, greater than 14 wt %, greater than 19 wt %, greater than 25 wt %, or greater than 34 wt %. In some embodiments, higher water concentrations, e.g., greater than 45 wt %, and lower water concentrations, e.g., less than 2.5 wt %, may also be contemplated.

In some embodiments, the concentration of acetonitrile in the first distillate stream ranges from 35 wt % to 95 wt %, e.g., from 35 wt % to 71 wt %, from 41 wt % to 77 wt %, from 47 wt % to 83 wt %, from 53 wt % to 89 wt %, or from 59 wt % to 95 wt %. In terms of upper limits, the acetonitrile concentration in the first distillate stream can be less than 95 wt %, e.g., less than 89 wt %, less than 83 wt %, less than 77 wt %, less than 71 wt %, less than 65 wt %, less than 59 wt %, less than 53 wt %, less than 47 wt %, or less than 41 wt %. In terms of lower limits, the acetonitrile concentration in the first distillate stream can be greater than 35 wt %, e.g., greater than 41 wt %, greater than 47 wt %, greater than 53 wt %, greater than 59 wt %, greater than 65 wt %, greater than 71 wt %, greater than 77 wt %, greater than 83 wt %, or greater than 89 wt %. In some embodiments, higher acetonitrile concentrations, e.g., greater than 95 wt %, and lower acetonitrile concentrations, e.g., less than 35 wt %, may also be contemplated.

In some embodiments, the mass ratio of the acetonitrile in the first distillate stream to the water in the first distillate stream ranges from 3:1 to 12:1, e.g., from 3:1 to 6.9:1, from 3.4:1 to 7.9:1, from 4:1 to 9.1:1, from 4.6:1 to 10:1, or from 5.2:1 to 12:1. In terms of upper limits, the mass ratio of acetonitrile to water in the first distillate stream can be less than 12:1, e.g., less than 10:1, less than 9.1:1, less than 7.9:1, less than 6.9:1, less than 6:1, less than 5.2:1, less than 4.5:1, less than 4:1, or less than 3.4:1. In terms of lower limits, the mass ratio of acetonitrile to water in the first distillate stream can be greater than 3:1, e.g., greater than 3.4:1, greater than 4:1, greater than 4.5:1, greater than 5.2:1, greater than 6:1, greater than 6.9:1, greater than 7.9:1, greater than 9.1:1, or greater than 10.4:1. In some embodiments, higher mass ratios, e.g., greater than 12:1, and lower mass ratios, e.g., less than 3:1, may also be contemplated.

In some embodiments, the first bottoms stream further includes at least a portion of the methanol from the intermediate acetonitrile stream. The concentration of methanol in the first bottoms stream can range, for example, from 0.4 wt % to 9.6 wt %, e.g., from 0.4 wt % to 2.7 wt %, from 0.55 wt % to 3.7 wt %, from 0.76 wt % to 5.1 wt %, from 1 wt % to 7 wt %, or from 1.4 wt % to 9.6 wt %. In terms of upper limits, the methanol concentration in the first bottoms stream can be less than 9.6 wt %, e.g., less than 7 wt %, less than 5.1 wt %, less than 3.7 wt %, less than 2.7 wt %, less than 2 wt %, less than 1.4 wt %, less than 1 wt %, less than 0.76 wt %, or less than 0.55 wt %. In terms of lower limits, the methanol concentration in the first bottoms stream can be greater than 0.4 wt %, e.g., greater than 0.55 wt %, greater than 0.76 wt %, greater than 1 wt %, greater than 1.4 wt %, greater than 2 wt %, greater than 2.7 wt %, greater than 3.7 wt %, greater than 5.1 wt %, or greater than 7 wt %. In some embodiments, higher methanol concentrations, e.g., greater than 9.6 wt %, and lower methanol concentrations, e.g., less than 0.4 wt %, may also be contemplated.

In some embodiments, the first distillate stream further includes at least a portion of the methanol from the intermediate acetonitrile stream. The concentration of methanol in the first distillate stream can range, for example, from 1.2 wt % to 23 wt %, e.g., from 1.2 wt % to 7.1 wt %, from 1.6 wt % to 9.5 wt %, from 2.2 wt % to 13 wt %, from 2.9 wt % to 17 wt %, or from 3.9 wt % to 23 wt %. In terms of upper limits, the methanol concentration in the first distillate stream can be less than 23 wt %, e.g., less than 17 wt %, less than 13 wt %, less than 9.5 wt %, less than 7.1 wt %, less than 5.3 wt %, less than 3.9 wt %, less than 2.9 wt %, less than 2.2 wt %, or less than 1.6 wt %. In terms of lower limits, the methanol concentration in the first distillate stream can be greater than 1.2 wt %, e.g., greater than 1.6 wt %, greater than 2.2 wt %, greater than 2.9 wt %, greater than 3.9 wt %, greater than 5.3 wt %, greater than 7.1 wt %, greater than 9.5 wt %, greater than 13 wt %, or greater than 17 wt %. In some embodiments, higher methanol concentrations, e.g., greater than 23 wt %, and lower methanol concentrations, e.g., less than 1.2 wt %, may also be contemplated.

In some embodiments, the mass ratio of the methanol in the first bottoms stream to the methanol in the first distillate stream ranges from 0.4:1 to 10:1, e.g., from 0.4:1 to 2.8:1, from 0.55:1 to 3.8:1, from 0.76:1 to 5.3:1, from 1.1:1 to 7.2:1, or from 1.4:1 to 10:1. In terms of upper limits, the mass ratio of the methanol in the first bottoms stream to the methanol in the first distillate stream can be less than 10:1, e.g., less than 7.2:1, less than 5.3:1, less than 3.8:1, less than 2.8:1, less than 2:1, less than 1.4:1, less than 1.1:1, less than 0.76:1, or less than 0.55:1. In terms of lower limits, the mass ratio of the methanol in the first bottoms stream to the methanol in the first distillate stream can be greater than 0.4:1, e.g., greater than 0.55:1, greater than 0.76:1, greater than 1.1:1, greater than 1.4:1, greater than 2:1, greater than 2.8:1, greater than 3.8:1, greater than 5.3:1, or greater than 7.2:1. In some embodiments, higher mass ratios, e.g., greater than 10:1, and lower mass ratios, e.g., less than 0.4:1, may also be contemplated.

In some embodiments, the first bottoms stream includes at least a portion of the allyl alcohol from the intermediate acetonitrile stream, such that the concentration of allyl alcohol in the first distillate stream is less than that in the intermediate acetonitrile stream. It can be beneficial for the provided separation process to remove the allyl alcohol of the intermediate acetonitrile stream in the first distillation, rather than in later unit operations, to realize energy and cost efficiencies, and to provide a final acetonitrile product stream having a higher acetonitrile product purity.

The concentration of allyl alcohol in the first bottoms stream can range, for example, from 0 to 1 wt %, e.g., from 0 to 0.6 wt %, from 0.1 wt % to 0.7 wt %, from 0.2 wt % to 0.8 wt %, from 0.3 wt % to 0.9 wt %, or from 0.4 wt % to 1 wt %. In terms of upper limits, the allyl alcohol concentration in the first bottoms stream can be less than 1 wt %, e.g., less than 0.9 wt %, less than 0.8 wt %, less than 0.7 wt %, less than 0.6 wt %, less than 0.5 wt %, less than 0.4 wt %, less than 0.3 wt %, less than 0.2 wt %, or less than 0.1 wt %. In terms of lower limits, the allyl alcohol concentration in the first bottoms stream can be greater than 0.1 wt %, e.g., greater than 0.2 wt %, greater than 0.3 wt %, greater than 0.4 wt %, greater than 0.5 wt %, greater than 0.6 wt %, greater than 0.7 wt %, greater than 0.8 wt %, or greater than 0.9 wt %. In some embodiments, higher allyl alcohol concentrations, e.g., greater than 1 wt %, may also be contemplated.

The concentration of allyl alcohol in the first distillate stream can range, for example, from 0 wt % to 0.05 wt %, e.g., from 0 wt % to 0.03 wt %, from 0.005 wt % to 0.035 wt %, from 0.01 wt % to 0.04 wt %, from 0.015 wt % to 0.045 wt %, or from 0.02 wt % to 0.05 wt %. In terms of upper limits, the allyl alcohol concentration in the first distillate stream can be less than 0.05 wt %, e.g., less than 0.045 wt %, less than 0.04 wt %, less than 0.035 wt %, less than 0.03 wt %, less than 0.025 wt %, less than 0.02 wt %, less than 0.015 wt %, less than 0.01 wt %, or less than 0.005 wt %. In terms of lower limits, the allyl alcohol concentration in the first distillate stream can be greater than 0 wt %, e.g., greater than 0.005 wt %, greater than 0.01 wt %, greater than 0.015 wt %, greater than 0.02 wt %, greater than 0.025 wt %, greater than 0.03 wt %, greater than 0.035 wt %, greater than 0.04 wt %, or greater than 0.045 wt %. In some embodiments, higher allyl alcohol concentrations, e.g., greater than 0.05 wt %, may also be contemplated.

In some embodiments, the mass ratio of the acetonitrile in the first distillate stream to the allyl alcohol in the first distillate stream ranges from 1000:1 to 100,000:1, e.g., from 1000:1 to 16,000:1, from 1600:1 to 25,000:1, from 2500:1 to 40,000:1, from 4000:1 to 63,000:1, or from 6300:1 to 100,000:1. In terms of upper limits, the mass ratio of acetonitrile to allyl alcohol in the first distillate stream can be less than 100,000:1, e.g., less than 63,000:1, less than 40,000:1, less than 25,000:1, less than 16,000:1, less than 10,000:1, less than 6300:1, less than 4000:1, less than 2500:1, or less than 1600:1. In terms of lower limits, the mass ratio of acetonitrile to allyl alcohol in the first distillate stream can be greater than 1000:1, e.g., greater than 1600:1, greater than 2500:1, greater than 4000:1, greater than 6300:1, greater than 10,000:1, greater than 16,000:1, greater than 25,000:1, greater than 40,000:1, or greater than 63,000:1. In some embodiments, higher mass ratios, e.g., greater than 100,000:1, and lower mass ratios, e.g., less than 10,000:1, may also be contemplated.

In some embodiments, the first bottoms stream further includes at least a portion of the oxazole from the intermediate acetonitrile stream. The concentration of oxazole in the first bottoms stream can range, for example, from 0 wt % to 0.1 wt %, e.g., from 0 wt % to 0.06 wt %, from 0.01 wt % to 0.07 wt %, from 0.02 wt % to 0.08 wt %, from 0.03 wt % to 0.09 wt %, or from 0.04 to 0.1 wt %. In terms of upper limits, the oxazole concentration in the first bottoms stream can be less than 0.1 wt %, e.g., less than 0.09 wt %, less than 0.08 wt %, less than 0.07 wt %, less than 0.06 wt %, less than 0.05 wt %, less than 0.04 wt %, less than 0.03 wt %, less than 0.02 wt %, or less than 0.01 wt %. In terms of lower limits, the oxazole concentration in the first bottoms stream can be greater than 0 wt %, e.g., greater than 0.01 wt %, greater than 0.02 wt %, greater than 0.03 wt %, greater than 0.04 wt %, greater than 0.05 wt %, greater than 0.06 wt %, greater than 0.07 wt %, greater than 0.08 wt %, or greater than 0.09 wt %. In some embodiments, higher oxazole concentrations, e.g., greater than 1 wt %, may also be contemplated.

The first distillate stream exiting the first distillation is purified to yield a product acetonitrile stream and a recycle stream. The product acetonitrile stream includes at least a portion of the acetonitrile from the first distillate stream. The product acetonitrile stream is a purified stream of acetonitrile isolated from the majority of other components of the feedstock stream. As a result, the concentration of acetonitrile in the product acetonitrile stream is very high. The concentration of acetonitrile in the product acetonitrile stream can range, for example, from 98 wt % to 99.99 wt %, e.g., from 98 wt % to 99.92 wt %, from 98.82 wt % to 99.95 wt %, from 99.31 wt % to 99.97 wt %, from 99.59 wt % to 99.98 wt %, or from 99.76 wt % to 99.99 wt %. In terms of lower limits, the acetonitrile concentration in the product acetonitrile stream can be greater than 98 wt %, e.g., greater than 98.83 wt %, greater than 99.31 wt %, greater than 99.59 wt %, greater than 99.76 wt %, greater than 99.86 wt %, greater than 99.92 wt %, greater than 99.95 wt %, greater than 99.97 wt %, greater than 99.98 wt %, or greater than 99.99 wt %.

Second Distillation

In some embodiments, the purification of the first distillate stream of the provided separation process includes the distillation of the first distillate stream in a second distillation column to yield a second distillate stream and a second bottoms stream. The second distillate stream includes at least a portion of the methanol from the first distillate stream. The second bottoms stream includes at least a portion of the acetonitrile from the first distillate stream.

The structure of the second distillation column can vary widely according to designs known to those of ordinary skill in the art, and any suitable column can be employed as long as the separation specifications described herein are achieved. For example the second distillation column can include any suitable separation device or combination of separation devices. The second distillation column can include a column, e.g., a standard distillation column, an extractive distillation column and/or an azeotropic distillation column. In some cases, the term "second distillation column" refers to multiple distillation columns configured to operate in conjunction with one another.

The second distillation column is configured to operate at a low pressure selected to provide the separation specifications disclosed herein. In some embodiments, the low pressure operation of the second distillation column includes applying cooling to better enable the creation of a stronger vacuum. In some embodiments, the cooling includes delivering chilled water to the unit operation of the second distillation column.

In some embodiments, the second distillation column is operated at a pressure ranging from 100 kPa to 200 kPa, e.g., from 105 kPa to 200 kPa, from 110 kPa to 200 kPa, from 110 kPa to 175 kPa, from 110 kPa to 150 kPa, or from 110 kPa to 125 kPa. In terms of upper limits, the second distillation column operating pressure can be less than 200 kPa, e.g., less than 190 kPa, less than 175 kPa, less than 150 kPa, less than 140 kPa, less than 135 kPa, less than 130 kPa, less than 125 kPa, less than 120 kPa, or less than 115 kPa. In terms of lower limits, the second distillation column operating pressure can be greater than 100 kPa, e.g., greater than 101 kPa, greater than 103 kPa, greater than 104 kPa, greater than 105 kPa, greater than 106 kPa, greater than 107 kPa, greater than 108 kPa, greater than 109 kPa, or greater than 110 kPa. In some embodiments, higher column pressures, e.g., greater than 200 kPa, and lower column pressures, e.g., less than 100 kPa, may also be contemplated.

In some embodiments the concentration of methanol in the second distillate stream ranges from 25 wt % to 90 wt %, e.g., from 25 wt % to 64 wt %, from 31.5 wt % to 70.5 wt %, from 38 wt % to 77 wt %, from 44.5 wt % to 83.5 wt %, or from 51 wt % to 90 wt %. In terms of upper limits, the methanol concentration in the second distillate stream can be less than 90 wt %, e.g., less than 83.5 wt %, less than 77 wt %, less than 70.5 wt %, less than 64 wt %, less than 57.5 wt %, less than 51 wt %, less than 44.5 wt %, less than 38 wt %, or less than 31.5 wt %. In terms of lower limits, the methanol concentration in the second distillate stream can be greater than 25 wt %, e.g., greater than 31.5 wt %, greater than 38 wt %, greater than 44.5 wt %, greater than 51 wt %, greater than 57.5 wt %, greater than 64 wt %, greater than 70.5 wt %, greater than 77 wt %, or greater than 83.5 wt %. In some embodiments, higher methanol concentrations, e.g., greater than 90 wt %, and lower methanol concentrations, e.g., less than 25 wt %, may also be contemplated.

In some embodiments, the concentration of acetonitrile in the second bottoms stream ranges from 40 wt % to 95 wt %, e.g., from 40 wt % to 73 wt %, from 45.5 wt % to 78.5 wt %, from 51 wt % to 84 wt %, from 56.5 wt % to 89.5 wt %, or from 62 wt % to 95 wt %. In terms of upper limits, the acetonitrile concentration in the second bottoms stream can be less than 95 wt %, e.g., less than 89.5 wt %, less than 84 wt %, less than 78.5 wt %, less than 73 wt %, less than 67.5 wt %, less than 62 wt %, less than 56.5 wt %, less than 51 wt %, or less than 45.5 wt %. In terms of lower limits, the acetonitrile concentration in the second bottoms stream can be greater than 40 wt %, e.g., greater than 45.5 wt %, greater than 51 wt %, greater than 56.5 wt %, greater than 62 wt %, greater than 67.5 wt %, greater than 73 wt %, greater than 78.5 wt %, greater than 84 wt %, or greater than 89.5 wt %. In some embodiments, higher acetonitrile concentrations, e.g., greater than 95 wt %, and lower acetonitrile concentrations, e.g., less than 40 wt %, may also be contemplated.

In some embodiments, the concentration of allyl alcohol in the second bottoms stream ranges from 0 wt % to 0.25 wt %, e.g., from 0 wt % to 0.04 wt %, from 0.004 wt % to 0.063 wt %, from 0.0063 wt % to 0.1 wt %, from 0.01 wt % to 0.16 wt %, or from 0.016 wt % to 0.25 wt %. In terms of upper limits, the allyl alcohol concentration in the second bottoms stream can be less than 0.25 wt %, e.g., less than 0.16 wt %, less than 0.1 wt %, less than 0.063 wt %, less than 0.03 wt %, less than 0.025 wt %, less than 0.016 wt %, less than 0.01 wt %, less than 0.0063 wt %, or less than 0.004 wt %. In terms of lower limits, the allyl alcohol concentration in the second bottoms stream can be greater than 0 wt %, e.g., greater than 0.0025 wt %, greater than 0.004 wt %, greater than 0.0063 wt %, greater than 0.01 wt %, greater than 0.016 wt %, greater than 0.025 wt %, greater than 0.04 wt %, greater than 0.063 wt %, greater than 0.1 wt %, or greater than 0.16 wt %. In some embodiments, higher allyl alcohol concentrations, e.g., greater than 0.25 wt %, may also be contemplated.

Third Distillation

In some embodiments, the purification of the first distillate stream of the provided separation process further includes the distillation of the second bottoms stream in a third distillation column to yield the recycle stream and a third bottoms stream. The third bottoms stream includes at least a portion of the acetonitrile from the second bottoms stream.

The structure of the third distillation column can vary widely according to designs known to those of ordinary skill in the art, and any suitable column can be employed as long as the separation specifications described herein are achieved. For example the third distillation column can include any suitable separation device or combination of separation devices. The third distillation column can include a column, e.g., a standard distillation column, an extractive distillation column and/or an azeotropic distillation column. In some cases, the term "third distillation column" refers to multiple distillation columns configured to operate in conjunction with one another.

The third distillation column is configured to operate at a low pressure selected to provide the separation specifications disclosed herein. In some embodiments, the low pressure operation of the third distillation column includes applying cooling to better enable the creation of a stronger vacuum. In some embodiments, the cooling includes delivering chilled water to the unit operation of the third distillation column.

In some embodiments, the third distillation column is operated at a pressure ranging from 100 kPa to 550 kPa, e.g., from 100 kPa to 500 kPa, from 150 kPa to 500 kPa, from 200 kPa to 500 kPa, from 250 kPa to 500 kPa, or from 300 kPa to 500 kPa. In terms of upper limits, the third distillation column operating pressure can be less than 550 kPa, e.g., less than 540 kPa, less than 530 kPa, less than 525 kPa, less than 510 kPa, less than 505 kPa, less than 500 kPa, less than 490 kPa, less than 485 kPa, or less than 475 kPa. In terms of lower limits, the third distillation column operating pressure can be greater than 100 kPa, e.g., greater than 105 kPa, greater than 150 kPa, greater than 175 kPa, greater than 200 kPa, greater than 250 kPa, greater than 275 kPa, greater than 300 kPa, greater than 350 kPa, or greater than 375 kPa. In some embodiments, higher column pressures, e.g., greater than 550 kPa, and lower column pressures, e.g., less than 100 kPa, may also be contemplated.

In some embodiments, the concentration of acetonitrile in the third bottoms stream ranges from 45 wt % to 95 wt %, e.g., from 45 wt % to 75 wt %, from 50 wt % to 80 wt %, from 55 wt % to 85 wt %, from 60 wt % to 90 wt %, or from 65 wt % to 95 wt %. In terms of upper limits, the acetonitrile concentration in the third bottoms stream can be less than 95 wt %, e.g., less than 90 wt %, less than 85 wt %, less than 80 wt %, less than 75 wt %, less than 70 wt %, less than 65 wt %, less than 60 wt %, less than 55 wt %, or less than 50 wt %. In terms of lower limits, the acetonitrile concentration in the third bottoms stream can be greater than 45 wt %, e.g., greater than 50 wt %, greater than 55 wt %, greater than 60 wt %, greater than 65 wt %, greater than 70 wt %, greater than 75 wt %, greater than 80 wt %, greater than 85 wt %, or greater than 90 wt %. In some embodiments, higher acetonitrile concentrations, e.g., greater than 95 wt %, and lower acetonitrile concentrations, e.g., less than 40 wt %, may also be contemplated.

In some embodiments, the concentration of allyl alcohol in the third bottoms stream ranges from 0 wt % to 0.5 wt %, e.g., from 0 wt % to 0.08 wt %, from 0.008 wt % to 0.13 wt %, from 0.013 wt % to 0.2 wt %, from 0.02 wt % to 0.32 wt %, or from 0.032 wt % to 0.5 wt %. In terms of upper limits, the allyl alcohol concentration in the third bottoms stream can be less than 0.5 wt %, e.g., less than 0.32 wt %, less than 0.2 wt %, less than 0.13 wt %, less than 0.08 wt %, less than 0.05 wt %, less than 0.032 wt %, less than 0.02 wt %, less than 0.013 wt %, or less than 0.008 wt %. In terms of lower limits, the allyl alcohol concentration in the third bottoms stream can be greater than 0 wt %, e.g., greater than 0.008 wt %, greater than 0.013 wt %, greater than 0.02 wt %, greater than 0.032 wt %, greater than 0.05 wt %, greater than 0.08 wt %, greater than 0.13 wt %, greater than 0.2 wt %, or greater than 0.32 wt %. In some embodiments, higher allyl alcohol concentrations, e.g., greater than 0.25 wt %, may also be contemplated.

In some embodiments, the concentration of methanol in the recycle stream ranges from 0 wt % to 0.004 wt %, e.g., from 0 wt % to 0.0006 wt %, from 0.00006 wt % to 0.001 wt %, from 0.0001 wt % to 0.002 wt %, from 0.0002 wt % to 0.003 wt %, or from 0.0003 wt % to 0.004 wt %. In terms of upper limits, the methanol concentration in the recycle stream can be less than 0.004 wt %, e.g., less than 0.003 wt %, less than 0.002 wt %, less than 0.001 wt %, less than 0.0004 wt %, less than 0.0003 wt %, less than 0.0002 wt %, less than 0.0001 wt %, less than 0.00006 wt %, or less than 0.00004 wt %. In terms of lower limits, the methanol concentration in the recycle stream can be greater than 0 wt %, e.g., greater than 0.00004 wt %, greater than 0.00006 wt %, greater than 0.0001 wt %, greater than 0.0002 wt %, greater than 0.0003 wt %, greater than 0.0004 wt %, greater than 0.001 wt %, greater than 0.002 wt %, or greater than 0.003 wt %. In some embodiments, higher methanol concentrations, e.g., greater than 0.004 wt %, may also be contemplated.

Fourth Distillation

In some embodiments, the purification of the first distillate stream of the provided separation process further includes the distillation of the third bottoms stream in a fourth distillation column to yield the product acetonitrile stream. The product acetonitrile stream includes at least a portion of the acetonitrile from the third bottoms stream. The concentration of acetonitrile in the product acetonitrile stream can be as disclosed herein, e.g., ranging from 98 wt % to 99.9 wt %.

The structure of the fourth distillation column can vary widely according to designs known to those of ordinary skill in the art, and any suitable column can be employed as long as the separation specifications described herein are achieved. For example the fourth distillation column can include any suitable separation device or combination of separation devices. The fourth distillation column can include a column, e.g., a standard distillation column, an extractive distillation column and/or an azeotropic distillation column. In some cases, the term "fourth distillation column" refers to multiple distillation columns configured to operate in conjunction with one another.

The fourth distillation column is configured to operate at a low pressure selected to provide the separation specifications disclosed herein. In some embodiments, the low pressure operation of the fourth distillation column includes applying cooling to better enable the creation of a stronger vacuum. In some embodiments, the cooling includes delivering chilled water to the unit operation of the fourth distillation column.

In some embodiments, the fourth distillation column is operated at a pressure ranging from 10 kPa to 80 kPa, e.g., from 10 kPa to 35 kPa, from 12 kPa to 43 kPa, from 15 kPa to 53 kPa, from 19 kPa to 65 kPa, or from 23 kPa to 80 kPa. In terms of upper limits, the fourth distillation column operating pressure can be less than 80 kPa, e.g., less than 65 kPa, less than 53 kPa, less than 43 kPa, less than 35 kPa, less than 28 kPa, less than 23 kPa, less than 19 kPa, less than 15 kPa, or less than 12 kPa. In terms of lower limits, the fourth distillation column operating pressure can be greater than 10 kPa, e.g., greater than 12 kPa, greater than 15 kPa, greater than 19 kPa, greater than 23 kPa, greater than 28 kPa, greater than 35 kPa, greater than 43 kPa, greater than 53 kPa, or greater than 65 kPa. In some embodiments, higher column pressures, e.g., greater than 80 kPa, and lower column pressures, e.g., less than 10 kPa, may also be contemplated.

As used herein, "greater than" and "less than" limits may also include the number associated therewith. Stated another way, "greater than" and "less than" may be interpreted as "greater than or equal to" and "less than or equal to." It is contemplated that this language may be subsequently modified in the claims to include "or equal to." For example, "greater than 10" may be interpreted as, and subsequently modified in the claims as "greater than or equal to 10."

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims or the equivalents thereof.

Examples

The present disclosure will be better understood in view of the following non-limiting examples. The following examples are intended for illustrative purposes only and do not limit in any way the scope of the present disclosure.

FIG. 1 illustrates an exemplary separation scheme 100. As shown in the scheme, feedstock stream 101 is fed to a digester 102. The composition of the feedstock stream is shown in Table 1, and includes acetonitrile, methanol, hydrogen cyanide, water, allyl alcohol, oxazole, and propionitrile. A caustic feed, and in particular sodium hydroxide, may be combined with the feedstock stream to be co-fed to the digester 102 or the caustic feed may be separately introduced to the digester 102. The digester 102 treats the feedstock stream to remove hydrogen cyanide and produce an intermediate acetonitrile stream 103. The composition of the intermediate acetonitrile stream is shown in Table 1.

The intermediate acetonitrile stream 103 is fed to a first distillation column 104. Distillation of the intermediate acetonitrile stream in the first distillation column yields a first bottoms stream 105 and a first distillate stream 106. The composition of the first bottoms stream is shown in Table 1, and includes water and methanol from the intermediate acetonitrile stream. The composition of the second acetonitrile stream is shown in Table 1, and includes acetonitrile and methanol from the first acetonitrile intermediate stream.

The first distillate stream 106 is fed to a second distillation column 107. Distillation of the first distillate stream in the second distillation column yields a second distillate stream 108 and a second bottoms stream 109. The composition of the second distillate stream is shown in Table 1, and includes methanol from the first distillate stream. The composition of the third acetonitrile stream is shown in Table 1, and includes acetonitrile from the second acetonitrile intermediate stream.

The second bottoms stream 109 is fed to a third distillation column 110. Distillation of the second bottoms stream in the third distillation column yields a recycle stream 111 and a third bottoms stream 112. The composition of the recycle stream is shown in Table 1, and includes acetonitrile from the second bottoms stream. The composition of the fourth acetonitrile stream is shown in Table 1, and includes acetonitrile from the third acetonitrile intermediate stream.

The third bottoms stream 112 is fed to a fourth distillation column 113. Distillation of the third bottoms stream in the fourth distillation column yields a product acetonitrile stream 114. The composition of the product acetonitrile stream is shown in Table 1 in weight percent.

TABLE 1

Stream compositions of FIG. 1 separation process.

| Component | 101 | 103 | 105 | 106 | 108 | 109 | 111 | 112 | 114 |
|---|---|---|---|---|---|---|---|---|---|
| Hydrogen cyanide | 0.56 | 0 | 0 | 0 | 0 | 0 | 0 | 0 | 0 |
| Methanol | 3.28 | 3.28 | 2.08 | 5.74 | 59.52 | 0 | 0 | 0 | 0 |
| Oxazole | 0.44 | 0.44 | 0.01 | 2.18 | 17.92 | 0.50 | 0.86 | 0 | 0 |
| Acetonitrile | 8.00 | 8.00 | 0.09 | 70.83 | 10.50 | 77.27 | 75.2 | 79.93 | 99.95 |
| Allyl Alcohol | 0.22 | 0.22 | 0.25 | 0.02 | 0 | 0.02 | 0.01 | 0.05 | 0 |
| Propionitrile | 0.22 | 0.22 | 0 | 0.94 | 0 | 1.04 | 0.13 | 2.31 | 0 |
| Water | 83.74 | 83.37 | 94.73 | 12.32 | 0.15 | 13.62 | 23.39 | 0 | 0 |
| Other impurities | 3.54 | 4.47 | 2.85 | 7.97 | 11.9 | 7.54 | 0.42 | 17.71 | 0.05 |

EMBODIMENTS

The following embodiments are contemplated. All combinations of features and embodiments are contemplated.

Embodiment 1

A process for producing acetonitrile, the process comprising: treating a feedstock stream comprising acetonitrile, methanol, hydrogen cyanide, and water to remove hydrogen cyanide and produce an intermediate acetonitrile stream comprising less than 1 wt % hydrogen cyanide; distilling the intermediate acetonitrile stream in a first distillation column to yield a first bottoms stream comprising water, and a first distillate stream comprising acetonitrile, wherein the first distillation column is operated at a pressure less than 150 kPa; and purifying the first distillate stream to yield a product acetonitrile stream and a recycle stream.

Embodiment 2

An embodiment of embodiment 1, wherein the feedstock stream comprises more than 50 wt % water and wherein the first distillate stream comprises less than 45 wt % water.

Embodiment 3

An embodiment of embodiment 1 or 2, wherein the feedstock stream and the first bottoms stream each further comprises allyl alcohol.

Embodiment 4

An embodiment of any of the embodiments of embodiment 1-3, wherein the first bottoms stream comprises from 0 to 1.0 wt % allyl alcohol.

Embodiment 5

An embodiment of embodiment 4, wherein the feedstock stream comprises more than 0.05 wt % allyl alcohol and wherein the first distillate stream comprises less than 0.05 wt % allyl alcohol.

Embodiment 6

An embodiment of embodiment 4 or 5, wherein the mass ratio of the acetonitrile in the first distillate stream to the allyl alcohol in the first distillate stream is greater than 1000:1.

Embodiment 7

An embodiment of any of the embodiments of embodiment 1-6, wherein the mass ratio of the acetonitrile in the first distillate stream to the water in the first distillate stream is greater than 3:1.

Embodiment 8

An embodiment of any of the embodiments of embodiment 1-7, wherein the treating comprises: digesting the feedstock stream in a digester, wherein sodium hydroxide and the feedstock stream are fed to the digester.

Embodiment 9

An embodiment of any of the embodiments of embodiment 1-8, wherein the feedstock stream and the first distillate stream each further comprises oxazole.

Embodiment 10

An embodiment of embodiment 9, wherein the feedstock stream comprises more than 0.09 wt % oxazole and wherein the first bottoms comprises less than 0.1 wt % oxazole.

Embodiment 11

An embodiment of any of the embodiments of embodiment 1-10, wherein the feedstock stream further comprises acrylonitrile.

Embodiment 12

An embodiment of any of the embodiments of embodiment 1-11, wherein the first distillation column is operated at a pressure less than 80 kPa.

Embodiment 13

An embodiment of any of the embodiments of embodiment 1-12, wherein the product acetonitrile stream comprises more than 98 wt % acetonitrile.

Embodiment 14

An embodiment of any of the embodiments of embodiment 1-13, wherein the purifying comprises: distilling the first distillate stream in a second distillation column to yield a second distillate stream comprising methanol, and a second bottoms stream comprising acetonitrile.

Embodiment 15

An embodiment of embodiment 14, wherein the second distillation column is operated at a pressure less than 200 kPa.

Embodiment 16

An embodiment of embodiment 14 or 15, wherein the second distillate stream comprises more than 25 wt % methanol.

Embodiment 17

An embodiment of any of the embodiments of embodiment 14-16, wherein the purifying comprises: distilling the second bottoms stream in a third distillation column to yield the recycle stream comprising acetonitrile, and a third bottoms stream comprising acetonitrile.

Embodiment 18

An embodiment of embodiment 17, wherein the third distillation column is operated at a pressure less than 550 kPa.

Embodiment 19

An embodiment of embodiment 17 or 18, wherein the purifying comprises: distilling the third bottoms stream in a fourth distillation column to yield the product acetonitrile stream

Embodiment 20

An embodiment of embodiment 19, wherein the fourth distillation column is operated at a pressure less than 80 kPa.

Embodiment 21

An embodiment of any of the embodiments of embodiment 1-20, wherein the feedstock stream comprises more than 0.7 wt % methanol.

Embodiment 22

An embodiment of embodiment 21, wherein the first bottoms stream and the first distillate stream each comprise methanol, and wherein the mass ratio of the methanol in the first bottoms stream to the methanol in the first distillate stream ranges from 0.4:1 to 10:1.

Embodiment 23

An embodiment of any of the embodiments of embodiment 1-22, wherein the feedstock comprises propionitrile.

While the invention has been described in detail, modifications within the spirit and scope of the invention will be readily apparent to those of skill in the art in view of the foregoing discussion, relevant knowledge in the art, and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetonitrile, the process comprising:
    digesting a feedstock stream comprising acetonitrile, methanol, hydrogen cyanide, and water to remove hydrogen cyanide in a digester to produce an intermediate acetonitrile stream comprising less than 1 wt % hydrogen cyanide;
    distilling the intermediate acetonitrile stream in a first distillation column to yield a first bottoms stream comprising water, and a first distillate stream comprising acetonitrile, wherein the first distillation column is operated at a pressure less than 150 kPa; and
    purifying the first distillate stream to yield a product acetonitrile stream and a recycle stream.

2. The process of claim 1, wherein the feedstock stream comprises more than 50 wt % water and wherein the first distillate stream comprises less than 45 wt % water.

3. The process of claim 1, wherein the feedstock stream and the first bottoms stream each further comprises from 0 to 1.0 wt. % allyl alcohol.

4. The process of claim 3, wherein the feedstock stream comprises more than 0.05 wt % allyl alcohol and wherein the first distillate stream comprises less than 0.05 wt % allyl alcohol.

5. The process of claim 3, wherein the mass ratio of the acetonitrile in the first distillate stream to the allyl alcohol in the first distillate stream is greater than 1000:1.

6. The process of claim 1, wherein the mass ratio of the acetonitrile in the first distillate stream to the water in the first distillate stream is greater than 3:1.

7. The process of claim 1, wherein sodium hydroxide and the feedstock stream are fed to the digester.

8. The process of claim 1, wherein the feedstock stream and the first distillate stream each further comprises oxazole.

9. The process of claim 8, wherein the feedstock stream comprises more than 0.09 wt % oxazole and wherein the first bottoms comprises less than 0.1 wt % oxazole.

10. The process of claim 1, wherein the feedstock stream further comprises acrylonitrile.

11. The process of claim 1, wherein the first distillation column is operated at a pressure less than 80 kPa.

12. The process of claim 1, wherein the product acetonitrile stream comprises more than 98 wt % acetonitrile.

13. The process of claim 1, wherein the purifying comprises:
    distilling the first distillate stream in a second distillation column to yield a second distillate stream comprising methanol, and a second bottoms stream comprising acetonitrile.

14. The process of claim 13, wherein the second distillation column is operated at a pressure less than 200 kPa.

15. The process of claim 13, wherein the second distillate stream comprises more than 25 wt % methanol.

16. The process of claim 13, wherein the purifying comprises:
    distilling the second bottoms stream in a third distillation column to yield the recycle stream comprising acetonitrile, and a third bottoms stream comprising acetonitrile.

17. The process of claim 16 wherein the third distillation column is operated at a pressure less than 550 kPa.

18. The process of claim 16, wherein the purifying comprises:
    distilling the third bottoms stream in a fourth distillation column to yield the product acetonitrile stream, wherein the fourth distillation column is operated at a pressure less than 80 kPa.

19. The process of claim 1, wherein the feedstock stream comprises more than 0.7 wt % methanol.

20. The process of claim 1, wherein the feedstock comprises propionitrile.

* * * * *